United States Patent
Deshpande et al.

(10) Patent No.: US 9,399,020 B2
(45) Date of Patent: Jul. 26, 2016

(54) HYDROPHILIC MATRIX BEADLET COMPOSITIONS WITH ENHANCED BIOAVAILABILITY

(71) Applicant: OmniActive Health Technologies Limited, Mumbai, Maharashtra (IN)

(72) Inventors: Jayant Deshpande, Charlottetown (CA); Subhrangsu Sengupta, Thane (IN); Pravin Nalawade, Thane (IN); Swapnil Khamborkar, Thane (IN)

(73) Assignee: OmniActive Health Technologies Limited, Mumbai (IN)

( * ) Notice: Subject to any disclaimer, the term of this patent is extended or adjusted under 35 U.S.C. 154(b) by 30 days.

(21) Appl. No.: 14/487,400

(22) Filed: Sep. 16, 2014

(65) Prior Publication Data

US 2015/0328158 A1 Nov. 19, 2015

(30) Foreign Application Priority Data

May 16, 2014 (IN) .......................... 1660/MUM/2014
Sep. 4, 2014 (WO) .................. PCT/IB2014/001734

(51) Int. Cl.
*A61K 9/50* (2006.01)
*A61K 9/14* (2006.01)
(Continued)

(52) U.S. Cl.
CPC . *A61K 9/146* (2013.01); *A23L 1/00* (2013.01); *A23L 1/0029* (2013.01); *A23L 1/30* (2013.01);
(Continued)

(58) Field of Classification Search
CPC .............. A23L 1/30; A23L 1/302; A23L 1/00; A61K 9/14
See application file for complete search history.

(56) References Cited

U.S. PATENT DOCUMENTS 3,998,753 A 12/1976 Antoshkiw et al.
4,670,247 A 6/1987 Scialpi
(Continued)

FOREIGN PATENT DOCUMENTS

EP 1 212 071 1/2007
WO 2005/067894 * 7/2005
(Continued)

OTHER PUBLICATIONS

Javeer et al., "Enhanced solubility and dissolution of simvastatin by HPMC-based solid dispersions prepared by hot melt extrusion and spray-drying method", Journal of Pharmaceutical Investigation, No. 43, pp. 471-480, 2013.
(Continued)

*Primary Examiner* — Carlos Azpuru
(74) *Attorney, Agent, or Firm* — Hamre, Schumann, Mueller & Larson, P.C.

(57) ABSTRACT

The instant invention provides hydrophilic matrix beadlet compositions that include at least one fat soluble nutrient and an effective amount of cellulose polymer with low viscosity. The invention also provides a process for the preparation of the hydrophilic matrix composition by employing a fluid bed system or extrusion spheronization technique. This hydrophilic matrix beadlet composition is comprised of at least 5% to about 25% carotenoid wherein free lutein is present in combination with zeaxanthin. The free flowing nature of the composition allows it to be compressed into tablets or to be filled into two piece capsules or blended as a dry premix for beverage applications. These hydrophilic matrix compositions exhibit desired dissolution characteristics and at least 1.6 times more bioavailability as compared with marketed reference formulations containing modified starch, thus making it advantageous for nutraceutical applications.

10 Claims, 6 Drawing Sheets

(51) Int. Cl.
*A61K 31/047* (2006.01)
*A23L 1/00* (2006.01)
*A23L 1/30* (2006.01)
*A23L 1/302* (2006.01)

(52) U.S. Cl.
CPC .............. *A23L 1/302* (2013.01); *A23L 1/3006* (2013.01); *A61K 9/14* (2013.01); *A61K 9/5036* (2013.01); *A61K 9/5089* (2013.01); *A61K 31/047* (2013.01)

(56) References Cited

U.S. PATENT DOCUMENTS

| | | | |
|---|---|---|---|
| 6,146,671 | A | 11/2000 | Catron et al. |
| 7,045,643 | B2 | 5/2006 | Estrella De Castro et al. |
| 7,097,868 | B2 | 8/2006 | Blatt et al. |
| 7,691,297 | B2 | 4/2010 | Schaffner |
| 8,211,471 | B2 | 7/2012 | Diguet et al. |
| 8,597,642 | B2 | 12/2013 | Diguet et al. |
| 8,680,161 | B2 | 3/2014 | Hitzfeld et al. |
| 9,247,765 | B2 * | 2/2016 | Deshpande ........... A23L 1/3002 |
| 2010/0098770 | A1 | 4/2010 | Ramalingam et al. |

FOREIGN PATENT DOCUMENTS

| | | |
|---|---|---|
| WO | WO 2005/067894 | 7/2005 |
| WO | 2009/022034 | 2/2009 |
| WO | 2012/139895 | 10/2012 |
| WO | WO 2013/053793 | 4/2013 |

OTHER PUBLICATIONS

Mitchell et al., "A Framework to Investigate Drug Release Variability Arising From Hypromellose Viscosity Specifications in Controlled Release Matrix Tablets", Journal of Pharmaceutical Sciences, vol. 97, No. 6, Jun. 2008, pp. 2277-2285.
International Search Report for Application No. PCT/IB2014/001734, dated Jan. 26, 2015, 4 pages.
Written Opinion for International Application No. PCT/IB2014/001734, dated Jan. 26, 2015, 5 pages.

* cited by examiner

HYDROPHILIC MATRIX BEADLET COMPOSITIONS WITH ENHANCED BIOAVAILABILITY

FIELD OF THE INVENTION

The present invention relates to hydrophilic matrix compositions comprised of beadlets containing at least one fat soluble nutrient and effective amount of at least one cellulose polymer with low viscosity along with one more pharmaceutically acceptable excipient. The invention also relates to a process for preparation of these beadlets containing 5% to about 25% of said fat soluble nutrient. These compositions are comprised of fat soluble nutrients embedded in matrix of effective amount of low viscosity cellulose polymer along with at least one diluent or inert core to form beadlets. Such beadlets can be employed as beverage ingredient or formulated in dosage forms such as sachets for reconstitution and moulded as tablets or capsules for oral administration. These hydrophilic compositions exhibit enhanced bioavailability profile as compared with the marketed formulations containing carotenoids for nutraceutical applications.

BACKGROUND OF THE INVENTION

Beneficial health effects of certain fat soluble nutrients, such as, vitamins A, D, E and K, carotenoids, glycerides, fatty acids such as saturated and monounsaturated acids, capsaicin, Co-enzyme Q-10, Ubiquinol as well as curcumin are well known. These nutrients form an important part of the human diet. However, being lipophilic in nature, these nutrients are insoluble in water and pose serious absorption constraints with variable bioavailability profile. Hence development of compositions containing such nutrients is one of the most important areas which are being explored to a great extent.

Carotenoids are a family of yellow to orange-red terpenoid pigments synthesized by photosynthetic organisms and by many bacteria and fungi. They offer protection against oxidative damage and are responsible for the appearance of these colours in plants and animals. Carotenoids are also desirable commercial products used as additives and colorants in the food industry. Traditionally, carotenoids were obtained by extraction from plants or by direct chemical synthesis. They may be linear or have undergone ring closure at one or both ends. The ring structure(s) may carry hydroxy or keto groups. In all cases, the molecules are predominantly hydrophobic and are usually found in lipid domains of plant and animal tissues. Of the wide range of animal and vegetable foods that comprise the human diet, most contribute at least trace amounts of some of the 600 identified carotenoids and related compounds. However, only a few carotenoids from fruits and vegetables, are ingested in sufficient quantity to be detected in human plasma, the most abundant being beta-carotene, lutein, lycopene, alpha-carotene, beta-cryptoxanthin and zeaxanthin, along with their more common cis-isomers and some degradation products. Hence it is important to develop the formulations which would exhibit enhanced solubility and thus result in increased absorption in body fluids, to satisfy a daily requirement. Stability of these nutrients is also a concern due to their inherent chemical structure which is prone to oxidative and photogenic degradation; hence many efforts are also oriented towards getting stable formulations with robust processing steps which minimize the degradation.

Prior art references deal with numerous methods for preparing microencapsulated or coated compositions of fat soluble nutrients employing suitable excipients in order to increase stability and solubility.

U.S. Pat. No. 7,045,643 relates to a method for preparation of stable microcrystalline lutein formulations which involves dissolution of lutein in organic solvent in presence of antioxidants and vegetable oils, emulsifying and microencapsulating the organic solution with aqueous solution of modified starch using homogenization and evaporating until microcrystallization of lutein occurs. Modified starch such as octenyl succinate which is derived from waxy maize is used here to encapsulate lutein microcrystals. However such hydrophobically modified polymer and vegetable oil used in process of encapsulation may result in lower solubility of lutein microcrystals in body fluids, also the process for microencapsulation is costly and results in variable rate of active release from the formulation.

U.S. Pat. No. 3,998,753 demonstrates solubilization of carotenoids by preparing solutions of carotenoids in volatile organic solvents, such as halogenated hydrocarbons, and further emulsifying them with an aqueous solution of sodium lauryl sulphate in the presence of gelatine as the matrix.

U.S. Pat. No. 4,670,247 discloses the preparation of fat soluble beadlets by emulsifying a fat soluble active such as a vitamin, flavoring or aromatic substances with water, gelatin and a reducing sugar. The emulsion is then converted to droplets. The droplets are collected in a starch powder to form particles which are heat treated to form a water insoluble beadlet.

A gelatin matrix as used in the above prior art document results in beadlets which are water insoluble and hence may result in lower solubility of the active nutrient, thus affecting bioavailability.

However, polymers derived from animals may not be preferred in nutritional products; due to for example challenging acceptability by users and customers.

U.S. Pat. No. 6,146,671 discloses a method for a heat and/or oxygen-labile compound by encapsulation in a protective matrix of alginate and an additional polymeric material like gelatin, which provides a single layer coating system.

U.S. Pat. No. 7,097,868 relates to microencapsulated beadlet composition prepared by adding sodium/potassium alginate as an encapsulating polymer to a solution of lipophilic compound in the presence of a surface active agent and obtaining beadlets with improved stability. Even though sodium/potassium alginate may aid increased stability, its viscosity is at least 10 centipoise (cP) of 1% solution in water, further its concentration used in this invention (about 8 times of lipophilic compound) is very high which may lead to lag time for release of the active nutrient from such beadlet formulation. Further such systems may not be robust with respect to in vitro-in vivo co-relation because of a viscous matrix formed through which the active nutrient has to diffuse out for release in gastrointestinal tract (GIT), thus affecting subsequent absorption of the active nutrient, e.g. fat soluble nutrient.

U.S. Pat. No. 8,680,161 teaches compositions containing plant gums such as gum Arabic, gum Ghatti, at least one modified starch and one or more fat-soluble active ingredients, wherein the composition comprises less than 40 weight % oil. These compositions need a third coating layer for stability of beadlets. Particle size reduction of lipophilic compound was carried out in the presence of a surfactant which resulted in enhanced stability. However, a size reduction of lipophilic compounds may tend to agglomeration of the active and may also lead to increased cost making it resource sensitive.

U.S. Pat. No. 8,597,642 describes a multivitamin tablet formulation comprising a protective colloid of a modified starch like sodium octenyl succinate with maltodextrin, carbohydrates or gums along with an emulsifier.

Modified starches are made from starches substituted by known chemical methods with hydrophobic moieties. For example, starch may be treated with cyclic dicarboxylic acid anhydrides such as succinic anhydrides and substituted with a hydrocarbon chain.

The reference aims at use of hydrophobically modified starch derivatives for increasing absorption of fat soluble actives, which is not a desirable option as it may add further to the lipophilic property of the active ingredient, rendering it less soluble in a biological system.

U.S. Pat. No. 8,211,471 describes a process for the production of cross-linked beadlets wherein an emulsion of a carotenoid and vitamin A, polyunsaturated fatty acid, an emulsifier and a reducing sugar is prepared and converted to droplets, where these droplets are coated with finely dispersed calcium silicate powder. These beadlets are characterized by high stability and potency. However, these cross-linked beadlets are water insoluble and hence have limited bioavailability.

U.S. Pat. No. 7,691,297 relates to a process for the manufacture of beadlet preparations of fat-soluble substances in a water-soluble or water-dispersible non-gelling sulfonated lignin matrix along with corn starch wherein an aqueous emulsion of the fat-soluble substance(s) and the matrix component are fed through a spray nozzle. In recent years, the rheological properties of the sulfonated lignin especially at the lower pH, has become an area of concern. This negative viscosity behaviour of sulfonated lignins may need to be tackled in such systems to get robust composition with desired solubility profile.

European Patent EP1212071B1 describes beadlets comprising xanthophylls and carotenes and/or retinoids, as well as dietary supplements comprising these beadlets and their methods of use. The particles of xanthophylls are embedded in a highly viscous gelatin-sucrose matrix. Upon oral administration of the developed formulation, the xanthophylls get released in the gastro-intestinal-tract from these formulations, in a slow and erratic fashion due to lower solubility and consequently the bioavailability of the composition is significantly reduced.

Patent application WO2009022034A1 describes manufacturing carotenoid compositions by dissolving a carotenoid in an organic solvent, emulsifying the resulting solution into an aqueous solution of a protective colloid and subsequently removing the solvent from this emulsion. The disadvantage of this process is the use of chlorinated hydrocarbons as the solvent for the active nutrient and its subsequent removal which is an environmental burden, thus making the process extremely expensive from a commercial point of view.

European patent application EP2696704A1 teaches a process for the manufacture of a lutein powder formulation comprising the steps of providing an aqueous solution/suspension of a polysaccharide; adding lutein in a modified polysaccharide solution/suspension and milling the suspension followed by drying the suspension. These modified polysaccharides such as glucose (syrup) and modified food starch contain a lipophilic moiety, e.g. a hydrocarbon moiety having a chain length of preferably 5 to 18 carbon atoms in the straight chain.

The formulations either aim at increasing stability by using a combination of antioxidants and emulsifier or at increasing solubility by employing encapsulating polymers such as reducing sugars, gelatin, sodium alginate, polysaccharide or modified starch derivatives. Particle size reduction is also carried out by grinding with a surfactant, thus focusing on increased solubility. These polymeric systems employ polymers which are either hydrophobic in nature or have considerable/higher viscosity at the concentrations used in the composition, thus affecting the resultant solubility.

Hence there is a need for alternative and improved stable beadlet formulations of fat soluble nutrients with an enhanced solubility and bioavailability profile. Such formulations should demonstrate good in vitro-in vivo co-relation, thus minimizing variable inter-personal absorption profiles.

Objectives of the Present Invention

Hence there is a need for alternative and improved stable beadlet formulations of fat soluble nutrients with an enhanced solubility and bioavailability profile. Such formulations should demonstrate good in vitro-in vivo co-relation, thus minimizing variable inter-personal absorption profiles.

The present invention addresses this need and discloses, after rigorous experimentation, matrix formulations of fat soluble nutrients that exhibit enhanced bioavailability. These beadlet compositions employ an effective amount of at least one hydrophilic cellulose polymer and at least one or more pharmaceutically acceptable excipient. Beadlets of the instant invention have a high loading capacity with respect to the active ingredient/nutrient and are comprised of one or more fat soluble nutrients embedded in a matrix of low viscosity cellulose polymeric excipient. Such stable beadlets can be employed for example as a beverage ingredient or be formulated for example in dosage forms, such as sachets for reconstitution and/or moulded as tablets or capsules for oral administration.

By "effective amount", effective amount is meant as an amount of hydrophilic polymer which is desired to be added in a matrix to impart hydrophilic characteristics to the composition.

The main objective of the present invention is to provide a hydrophilic matrix beadlet formulation of one or more fat soluble nutrients which exhibit enhanced bioavailability.

Another objective of the present invention is to prepare hydrophilic matrix beadlet compositions comprising of at least one fat soluble nutrient such as a carotenoid and an effective amount of at least one polymer with low viscosity. In some embodiments, the polymer with low viscosity is a cellulose type polymer. In some embodiments, the polymer with low viscosity is a non-cellulose type polymer. In some embodiments, the polymer with low viscosity has a viscosity of 1 to 5 cPs.

It will be appreciated that use of cellulose and/or non-cellulose low viscosity polymers in a hydrophilic matrix may be employed. Examples of such low viscosity polymers are described further below.

Yet another objective of the invention is to prepare hydrophilic matrix beadlets of one or more fat soluble nutrients wherein at least one low viscosity cellulose polymer is combined with at least one pharmaceutically acceptable excipient.

Yet further objective of the present invention is to provide hydrophilic matrix beadlet compositions containing at least 5% to about 25% of at least one fat soluble nutrient such as a carotenoid.

Yet another objective of the present invention is to provide a stable hydrophilic matrix beadlet carotenoid composition comprised of free Lutein and/or zeaxanthin and/or neoxanthin and/or α-cryptoxanthin and/or β-cryptoxanthin and/or mesozeaxanthin in combinations thereof with other lipophilic nutrients.

One more objective of the instant invention is to provide a hydrophilic matrix in which carotenoids are embedded in an effective amount of low viscosity cellulose polymer and at least one pharmaceutically acceptable excipient such as inert core or diluent to form beadlets.

Another objective of the instant invention is to prepare hydrophilic beadlets containing a ratio of carotenoids to low viscosity polymeric excipient, such as a ratio of 1:0.5 to 1:1.5 to form a matrix.

Yet another objective of the instant invention is to provide hydrophilic beadlets in which at least one low viscosity cellulose polymer has the viscosity in the range of 1 to 5 cP.

Yet another objective of the instant invention is to provide hydrophilic matrix beadlets which are prepared by fluid bed drying or extrusion spheronization.

One more objective of the instant invention is to employ carotenoid beadlets as a beverage ingredient or formulated in dosage forms such as sachets for reconstitution and/or moulded as tablets and/or capsules for oral administration.

Still one more embodiment of the present invention is to prepare hydrophilic matrix beadlets which exhibit desired dissolution characteristics and an enhanced bioavailability profile.

SUMMARY OF THE INVENTION

The instant invention provides hydrophilic matrix beadlet compositions with enhanced bioavailability. The matrix beadlets are comprised of at least one fat soluble nutrient and effective amount of at least one polymer with low viscosity (e.g. cellulose polymer) along with one or more pharmaceutically acceptable excipients, such as inert core and/or diluent. A hydrophilic matrix beadlet composition in one example is comprised of carotenoid wherein free lutein is present in combination with zeaxanthin and/or neoxanthin and/or α-cryptoxanthin and/or β-cryptoxanthin and/or mesozeaxanthin along with other excipients and antioxidants. These beadlets contain at least 5% to about 25% of said carotenoid nutrient(s). Such beadlets are resistant to oxidation and get readily dispersed and dissolved in media under test by forming a homogenous yellow to orange coloured dispersion. The free flowing nature of said composition allows it to be compressed into tablets, or to be filled into two piece capsules or to be blended as a dry premix for beverage applications. The present invention also provides a process for the preparation of the hydrophilic matrix beadlet formulation by employing a fluid bed system with a top/tangential/bottom spray technique or by extrusion spheronization. These hydrophilic compositions exhibit desired dissolution characteristics and an enhanced bioavailability profile as compared to marketed formulations containing carotenoids for nutraceutical applications.

DETAILED DESCRIPTION OF THE INVENTION

The invention relates to hydrophilic matrix beadlet formulations of fat soluble nutrients and methods for preparation of such beadlets.

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The fat soluble nutrients suitable for the instant invention are sensitive to heat or oxygenating conditions. Non-limiting examples are carotenoids, fat soluble vitamins, fatty acids, glycerides, capsaicin, curcumin and mixtures thereof.

Preferably the fat soluble nutrient is selected from the group such as, but not limited to, carotenoids (especially alpha-carotene, beta-carotene, 8'-apo-beta-carotenal, 8'-apo-beta-carotenoic acid esters such as the ethyl ester, canthaxanthin, astaxanthin, astaxanthin ester, betacryptoxanthin, lycopene, lutein, lutein (di) ester, zeaxanthin or crocetin, mesozeaxanthin, alpha or beta-zeacarotene or mixtures thereof), vitamins (A, D, E, K, CoQ 10) or derivatives thereof (such as their acetates, e.g. vitamin A acetate or tocopherol acetate, or their longer chain fatty acid esters, e.g. vitamin A palmitate or tocopherol palmitate), capsaicin, dihydrocapsaicin, derivatives thereof, polyunsaturated fatty acids (PUFAs) or derivatives thereof, and triglycerides rich in polyunsaturated fatty acids such as eicosapentaenoic acid (EPA), docosahexaenoic acid (DHA) or gamma-linolenic acid (GLA), Omega 3, Omega 6 oils or derivatives thereof, ethanolic extracts of Terminalia, Salacia and/or mixtures thereof. Further fat soluble nutrient compounds suitable for the present invention are compounds which may have a taste or smell that may be desired to be masked, e.g., bitter tasting vitamins and fish oil.

More preferably, the fat-soluble nutrients of the instant invention are selected from the carotenoids such as, but not limited to, beta-carotene, lutein, lycopene, astaxanthin, astaxanthin ester, zeaxanthin, neoxanthin, α-cryptoxanthin, β-cryptoxanthin and canthaxanthin. Further carotenoids are most preferably used in combination of free lutein with zeaxanthin and/or neoxanthin and/or α-cryptoxanthin and/or β-cryptoxanthin and the like or the mixtures thereof. Throughout the description the term fat soluble nutrients encompasses the foregoing definition and mixtures of said compounds.

According to one of the embodiments of the present invention, carotenoids of the present invention are obtained from Marigold flowers and employed in combination of free lutein and zeaxanthin, more preferably t-lutein and zeaxanthin. The ratio in which they are used in instant invention varies from 4.5:1 to 5.5:1. More preferably these carotenoids are used in the ratio of 5:1.

According to the instant invention, it is surprisingly found that when matrix beadlets of fat soluble nutrients are prepared using low viscosity cellulose polymer, resulting beadlets exhibit hydrophilic properties. Such beadlets are stable and easily dispersible in aqueous system, resulting into dark yellow to orange coloured solution, which is desirable for its application in the beverage application. Further these beadlets have good flow properties, which can be either filled in capsules or compressed in the form of tablets. Hydrophilic matrix beadlets of the invention exhibit a desired drug release profile and an enhanced bioavailability, which is at least 1.6 times higher than marketed formulations.

According to one embodiment, the instant invention relates to hydrophilic matrix beadlet compositions of fat soluble nutrients like carotenoids, which are comprised of an effective amount of a polymeric matrix excipient with low viscosity and at least one more pharmaceutically acceptable excipient.

In accordance with another embodiment of the present invention, a new matrix system is provided which acts as an immediate release composition in the form of hydrophilic beadlets of fat soluble nutrients.

Beadlets are the systems comprised of coated or uncoated core, wherein carotenoid active ingredient(s)/nutrient(s) are dispersed or embedded in an effective amount of low viscosity cellulose polymer and at least one or more pharmaceutically acceptable excipient to form a core.

In one of the embodiments of the invention, a core of the beadlets is comprised of a matrix of carotenoid, which is a combination of free lutein and zeaxanthin, formed in the presence of an effective amount of low viscosity polymeric excipient, thus imparting hydrophilic property to the core matrix.

In one more embodiment, the low viscosity cellulose polymeric excipient is selected from the group such as, but not limited to, carboxymethyl cellulose, methyl cellulose, hydroxyethyl cellulose, hydroxypropyl cellulose, hydroxypropyl methyl cellulose, methyl ethyl cellulose, hydroxyl ethyl methyl cellulose, sodium carboxy methyl cellulose, and the like, and combinations thereof.

It will also be appreciated that non-cellulose polymers may be employed include for example but not limited to one or more of copovidone and hydroxypropyl methyl acrylamide, and the like.

Low viscosity polymeric excipient of the invention is a polymer (e.g. may be a cellulose polymer), which exhibits viscosity of 1 to 5 cP, such as for example when about 1-2% w/v of solution is prepared in water and is hydrophilic in nature. It will be appreciated that the viscosity can vary as desired and/or suitable for any one or more of the polymers herein, when a concentration of about 1 to 2% w/v of solution is prepared for example in water to result in a viscosity of 1 to 5 cP.

As per some embodiments of the instant invention, the low viscosity cellulose polymeric excipient may be hydroxypropyl methyl cellulose (HPMC).

As per some embodiments of this invention, low viscosity cellulose polymer excipient is hydroxypropyl methyl cellulose (HPMC) having viscosity of about 2.5 cps, for example when about 2% w/v polymer solution is prepared in water.

As per another embodiment of the invention, low viscosity cellulose polymeric excipient is used in an effective amount in the present invention. Effective amount of low viscosity cellulose polymer means the amount so that it forms a matrix and carotenoids get embedded in this polymeric excipient; wherein it confers upon its own hydrophilic properties to fat soluble nutrient.

The amount of low viscosity cellulose polymer excipient incorporated into the beadlets is such that it is effective to impart its hydrophilic properties to the matrix core of the beadlets, thus increasing solubility of resultant beadlets. In certain preferred embodiments of the present invention, the low viscosity HPMC is included in the beadlets so that ratio of carotenoid to such polymer is 1:0.5 to 1:1.5. It will be appreciated that the ratio of carotenoid to low viscosity polymer is by weight percentage w/w.

As per one more embodiment, the amount of low viscosity HPMC used may range from at or about 3% to at or about 40% w/w of the beadlets. In some embodiments, the amount of low viscosity cellulosic polymer as employed may range from at or about 6% to at or about 30% w/w of the beadlets.

As per one more important embodiment of the present invention, the amount of carotenoid, used in the beadlets varies from at or about 2% to at or about 45% w/w of the beadlets, more preferably at or about 5% to at or about 30% w/w of the beadlets. Preferably these beadlets contain carotenoids, which is present in the form of combination of free lutein and zeaxanthin.

According to further embodiment of the invention, a size of the hydrophilic matrix beadlets is at or about 10 microns to at or about 400 microns. In some embodiments, the size of the hydrophilic matrix beadlets is at or about 100 microns to at or about 400 microns.

Hydrophilic matrix beadlets of the instant invention are formed of carotenoids as fat soluble nutrients, an effective amount of low viscosity cellulose polymer and at least one or more pharmaceutically acceptable excipient.

Hydrophilic matrix beadlets of the present invention typically may also include other pharmaceutically acceptable excipients such as, but not limited to, inert cores, diluents, antioxidants, surfactants, binders, disintegrants, glidants, lubricants, solvents, coating agents, and the like. As is well known to those skilled in the art, pharmaceutical excipients are routinely incorporated into solid dosage forms. This is done to ease the manufacturing process as well as to improve the performance of the dosage form.

In an embodiment of this invention, the inert core may be comprised of any material such as, but not limited to, sugar (e.g Sprayspheres® or Pharm-A-Spheres® etc.), microcrystalline cellulose (Cellets® and Vivapur® MCC), tartaric acid, mannitol, starch and the like or combinations thereof and that are commercially available under different trade names. More preferably, the inert core is selected from the material such as, but not limited to, sugar or mannitol. The inert core employed is generally in the form of a sphere, and can have a diameter from about 200 microns to about 3 mm. In a fluidization process; the medium of coating can either be aqueous or organic.

As per one embodiment of the instant invention, examples of suitable diluents include, but are not limited to, starch, dicalcium phosphate, microcrystalline cellulose, lactose monohydrate, dextrate hydrated, colloidal grade carboxymethyl cellulose sodium, carboxymethyl cellulose calcium and other cellulose containing polymers and their derivatives or the like and mixtures thereof. Preferably, a suitable diluent is selected from conventional marketed grades of microcrystalline cellulose, including, but not limited to Avicel®PH 101, Avicel®PH 102, Avicel®PH 103, Avicel®PH 105, Avicel®PH 112, Avicel®PH 113, Avicel® PH 300, Avicel®PH 212, Avicel® PH 301, Avicel® PH 302, and the like or mixtures thereof.

As per another embodiment of the instant invention, the antioxidant is selected from commonly used excipients including, but not limited to α-Tocopherol, β-Tocopherol, γ-Tocopherol, mixture of Tocopherols, citric acid, Rosemary extract, ascorbyl palmitate, sodium ascorbate or the like and combinations thereof.

Suitable surfactants include, but are not limited to, anionic and non-ionic surfactants or a mixture thereof. The non-ionic surfactants employed in the composition may include, but are not limited to, ethoxylated fatty acid esters, ethoxylated fatty acid ethers, ethoxylated sorbitan ethers, ethoxylated alkylphenols, glycerol esters, glycerol sugar esters, polyoxyethylene glycerol monolaurate, polyoxyethylene glycerol monostearate, polyoxyethylene-20-cetyl stearate, polyoxyethylene-25-cetyl stearate, polyoxyethylene(25)-oxypropylene monostearate, polyoxyethylene-20-sorbitan monopalmitate, poly-oxyethylene-16-tert-octylphenol, polyoxyethylene-20-cetyl ether, polyethylene glycol(1000) monocetyl ether, ethoxylated castor oil, polyoxyethylene sorbitol-lanolin derivatives, polyoxyethylene(25)propylene glycol stearate, polyoxyethylenesorbitol esters, polyoxyethylene-20-sorbitan monopalmitate, polyoxyethylene-16-tert-octylphenol, polyoxyethylene-20-cetyl ether, glycyeryl undecylenate and Polysorbate 60, capmul (medium chain glyceride), peceol(glyceryl monooleate), glyceryl laurate and glyceryl caprylate (Capmul MCM), PEG sorbitan fatty acid esters like PEG-20 sorbitan monolaurate (Tween 20), PEG-20 sorbitan monostearate (Tween 60), PEG-20 sorbitan monooleate (Tween 80), sorbitan fatty acid esters like sorbitan monolaurate (Span 20), glyceryl stearate (Cithrol GMS) or the like and mixtures thereof. Suitable anionic surfactants include, but are not limited to, fatty alcohol sulfates, alpha olefin sulfonates, sulfosuccinates, phosphate esters, carboxylates, sarcosinates, alkyl benzene sulfonates, alkyl sulfonates, olefin sulfonates, alkyl ethersulfonates, glycerol ethersulfonates, alpha-methyl estersulfonates, sulfonic fatty acids, alkyl sulfates, fatty alcohol ethersulfates, glycerol ethersulfates, mixed hydroxy ethersulfates, monoglyceride (ether)sulfates, fatty acid amide(ether)sulfates, sulfosuccinates, sulfosuccinamates, sulfotriglycerides, alkyl oligoglycoside sulfates, alkyl(ether)phosphates or the like and mixtures thereof.

Suitable disintegrants employed in the compositions of the present invention include, but are not limited to croscarmellose sodium, sodium starch glycolate, starch, crosslinked polyvinyl pyrrolidone, crosslinked sodium carboxy methyl cellulose and the like or mixtures thereof.

Examples of suitable binders include, but are not limited to, starch, pregelatinized starch, polyvinyl pyrrolidone (PVP), copovidone, gum acacia, xanthan gum, gum tragacanth, cellulose derivatives, such as hydroxypropylmethyl cellulose (HPMC), hydroxypropyl cellulose (HPC) and carboxymethyl cellulose (CMC) and their salts. Their amount used may range from about 0.1% to about 10% of the weight of the pellets. It may be advantageous to mix the binding agent with the colloidal suspension prior to spraying the suspension in the fluid-bed system.

Examples of suitable lubricants include, but are not limited to, magnesium stearate, calcium stearate, stearic acid, talc, and sodium stearyl fumarate. Compositions of the present invention may optionally also include a glidant such as, but not limited to, colloidal silica, silica gel, precipitated silica, or combinations thereof.

According to another embodiment, the coating agents of the present invention are suitable for providing elegance and protection to the beadlets and are selected from examples of excipients such as, but not limited to starch, starch derivatives, cellulose, gelatin, polyvinyl alcohols, waxes, gums, sucrose esters and sugars or combinations thereof. According to still another embodiment, starch is selected from sources such as, but not limited to, cereals, tubers, roots, legumes and fruits.

The present invention includes a process for preparation of hydrophilic matrix beadlets wherein a carotenoid is dispersed in a non-polar solvent along with at least one or more excipient and homogenized to get a dispersion. Effective amount of low viscosity cellulose polymeric excipient is dispersed in a polar solvent followed by addition of a non-polar solvent under stirring to get a uniform system. This low viscosity polymer system is then added to the carotenoid dispersion and mixed well. The resulting solution is loaded on inert core by using bottom spray, top spray fluid bed processor or by tangential spray, top spray Flex Stream process to get the beadlets. These beadlets obtained are further coated with a starch system comprised of one or more antioxidants. The resulting coating solution is loaded on carotenoid beadlets by using bottom spray, top spray fluid bed processor or by tangential spray, top spray Flex Stream process.

The present invention includes a process for preparation of carotenoid hydrophilic matrix beadlets by an extrusion and spheronization method. As per this process, carotenoid is dispersed in a suitable solvent. The dispersion is further added to a blend of an effective amount of low viscosity cellulose polymer and at least one or more pharmaceutically acceptable excipient such as sugars, surfactants, binders and other excipients. The powder blend can be prepared in a rapid mixing granulator and/or planetary mixer. After uniform mixing, the granules are extruded and spheronized to form uniform beadlets. These uniform spheroidal beadlets core are further coated with starch and antioxidant coating system to form coating beadlets.

It will be appreciated that the term "uniform" beadlets refers to the size of beadlets obtained after extrusion spheronization, which in some examples can be found to be at or about 50 to 80 mesh (e.g. at or about 170 to 300 microns) in size. It will be appreciated that a size range of a resultant batch of beadlets may be narrow, and so can be referred to as uniform beadlets. When the size of beadlets is uniform, for example it may be advantageous in some instances such as for coating, for exhibiting free flow, and for filling into capsules.

In another preferred embodiment the solvent employed in the process for preparation of hydrophilic matrix beadlets may be selected from the group such as, but not limited to, acetone, hexane, ethyl acetate, isopropyl alcohol, ethanol, dichloromethane, methanol, and a mixture thereof, more preferably from acetone, ethanol, dichloromethane, isopropyl alcohol, and more preferably dichloromethane and isopropyl alcohol.

In a preferred embodiment the non-polar solvents which may be used for preparing the dispersion of fat soluble nutrient include, but are not limited to, methylene chloride, chloroform, petroleum ether (low boiling), petroleum ether (high boiling) and the like or the mixtures thereof.

In another preferred embodiment, the polar solvents, which may be used for preparing the solution of low viscosity polymeric excipient, include, but are not limited to, isopropyl alcohol, acetone, methanol, ethanol, acetonitrile or mixtures thereof.

The non-polar solvent and polar solvent can be used in varying ratios. For instance, the non-polar and polar solvents can be at a ratio of about 1:1 to about 0.1:1 and, in some cases, can comprise a mixture of methylene chloride and isopropyl alcohol at a ratio of about 1:1 to about 0.1:1. The non-polar and polar solvents can also be at a ratio of about 0.1:1 to about 2:1 and, in some cases, can comprise a mixture of methylene chloride and isopropyl alcohol at a ratio of about 0.2:1 to about 2:1. It will be appreciated that the ratios of non-polar to polar solvent are based on volume percentage.

The beadlets may be filled into hard shell capsules or compressed into a tablet to provide formulations administered in single or divided doses of from about 2 to 45 mg carotenoids, preferably from about 5 to about 30 mg carotenoids daily.

The tablet formulation can be prepared by using a conventional process generally used by a person skilled in the art by employing techniques such as direct compression, dry granulation or wet granulation. In the process of direct compression, these beadlets can be mixed with vitamin premix containing other vitamins such as vitamin A, B, C, D, E or derivatives thereof in an effective amount. Such a blend is then mixed with other pharmaceutically acceptable excipients such as a diluent, a disintegrant, and/or a binder and then lubricated well and compressed to get desirable hardness. In dry granulation, roller compaction of excipients and blending with beadlets is affected along with other excipients.

Hydrophilic matrix beadlets formulated according to the present invention allow for immediate release of carotenoids and exhibit a desired drug release profile, wherein at least 90% of lutein is released over a period of the first 10 minutes. See e.g. FIG. 7, which is further described below.

According to another embodiment, a comparative bioavailability study of the composition of the present invention is evaluated along with a marketed reference product in healthy human volunteers under fed conditions.

The present invention is also applicable to combinations of carotenoids with other fat soluble nutrients. In one embodiment, compositions of the present invention comprise carotenoids in combination with other fat soluble nutrients selected from, but not limited to, fat soluble vitamins, fatty acids and glycerides.

In a further embodiment, hydrophilic matrix carotenoid beadlets of the present invention as an active ingredient or colorant or additives in may be used in a beverage application. The beadlets can be compressed into tablets or filled in two piece capsules or in sachets to be used as a dietary supplement in the pharmaceutical, nutraceutical, food, and cosmetic industries, and a method can comprise administering to the subject in need thereof hydrophilic matrix beadlet compositions of the present invention.

While the present invention has been described in terms of its specific illustrative embodiments, certain modifications and equivalents will be apparent to those skilled in the art and are intended to be included within the scope of the present invention. The details of the invention, its objects and advantages are explained hereunder in greater detail in relation to non-limiting exemplary illustrations.

EXAMPLES

Example 1

Preparation of Carotenoid Crystals

The preparation of carotenoid concentrate is described in Indian Patent Application No. 622/MAS/2002 (U.S. Pat. No. 6,737,535), the disclosures of which are incorporated by reference herein, and is summarized as follows.

Commercial grade marigold extract (57.98 g) containing 11.54% free lutein-zeaxanthin content (by spectrophotometric method) was mixed with potassium isopropyl alcoholate (prepared by dissolving 15 g potassium hydroxide in 175 ml isopropanol.) The saponification mixture was heated and maintained at 70° C. for a period of 3 hours. The degree of hydrolysis was monitored by HPLC during the saponification stage. Isopropanol was distilled off under reduced pressure and the solids obtained were stirred with 230 ml of water at room temperature. The mixture was taken into a reparatory funnel and extracted with equal volume of ethyl acetate (3 times). Ethyl acetate layer was collected and washed with distilled water for removing the excess alkali, soapy materials and other water-soluble impurities. The ethyl acetate layer was distilled off under reduced pressure to get saponified crude extract (25.01 g). This resultant crude extract (25.01 g) was subjected to purification by stirring with 100 ml of hexane/acetone mixture (80:20) at room temperature for 30 minutes, followed by filtration. The precipitate of carotenoid crystals obtained was washed with methanol. The resulting orange crystals were vacuum dried at ambient temperature for 72 hrs. The yield of the crystals was 3.41% (1.98 g). Carotenoid content was 86.23% by weight (as determined by UV/Vis spectrophotometry) out of which the contents of trans-lutein, zeaxanthin, and other carotenoids were 91.43%, 6.40% and 2.17% respectively as determined by HPLC analysis.

Example 2

Preparation of Hydrophilic Matrix Carotenoid Beadlets

TABLE 1

| | Composition of carotenoid matrix beadlets using formula 1 to 7 | | | | | | |
|---|---|---|---|---|---|---|---|
| Sr. No | Ingredients | Formula 1 | 2 | 3 | 4 | 5 | 6 | 7 |
| 1 | Carotenoids (Free Lutein + Zeaxanthin concentrate) | 10.08 | 10.08 | 10.43 | 10.08 | 10.08 | 10.08 | 47 |

TABLE 1-continued

Composition of carotenoid matrix beadlets using formula 1 to 7

| Sr. No | Ingredients | Formula 1 | 2 | 3 | 4 | 5 | 6 | 7 |
|---|---|---|---|---|---|---|---|---|
| 2 | Non pareil sugar | 25.64 | 54.86 | 48.58 | 46.95 | 49.5 | 0 | 10 |
| 3 | Microcrystalline cellulose | 0 | 0 | 0 | 0 | 0 | 49.5 | 0 |
| 4 | Low viscosity HPMC | 10.08 | 10.08 | 10.43 | 10.08 | 10.08 | 10.08 | 23.5 |
| 5 | Polyvinyl pyrrolidone | 29.23 | 0 | 0 | 0 | 0 | 0 | 0 |
| 6 | Ascorbyl Palmitate | 1.11 | 1.11 | 1.18 | 1.18 | 1.18 | 1.18 | 1 |
| 7 | Tween 80 | 0 | 0 | 7.55 | 7.55 | 5 | 5 | 2 |
| 8 | Crospovidone | 0 | 0 | 1.87 | 3.5 | 3.5 | 3.5 | 1.5 |
| 9 | Tocopherol mix | 3.16 | 3.16 | 3.28 | 3.23 | 3.23 | 3.23 | 2.3 |
| 10 | Sodium starch glycolate | 0.77 | 0.77 | 0 | 0 | 0 | 0 | 0 |
| 11 | Docusate Sodium | 4.02 | 4.02 | 0 | 0 | 0 | 0 | 0 |
| 12 | Sodium lauryl sulphate | 1.37 | 1.37 | 1.08 | 1.78 | 1.78 | 1.78 | 1.03 |
| 13 | Tapioca starch | 12.82 | 12.82 | 12.82 | 13.94 | 13.94 | 13.94 | 10 |
| 14 | Aerosil | 0 | 0 | 0.54 | 0 | 0 | 0 | 0 |
| 15 | Sodium Ascorbate | 1.05 | 1.06 | 1.04 | 1.04 | 1.04 | 1.04 | 1 |
| 16 | Talc | 0.67 | 0.67 | 1.21 | 0.67 | 0.67 | 0.67 | 0.67 |
| | Total | 100 | 100 | 100 | 100 | 100 | 100 | 100 |

Process for the Preparation Using Formula 1-5 and Formula 7:

Carotenoid is dispersed in non-polar solvent and a quantity of antioxidants, surfactants, disintegrants, binder is added to the carotenoid dispersion and then the carotenoid dispersion and binder are homogenised. Low viscosity HPMC polymer is dispersed in polar solvent followed by addition of non-polar solvent under stirring. Carotenoid dispersion was added to low viscosity HPMC system and mixed it completely. The resulting mixture is loaded on non pareil inert core by using bottom spray, top spray fluid bed processor or by tangential spray, top spray Flex Stream process and drug coating is completed. Beadlets obtained by the above process are further coated with a coating composition of starch and antioxidant by using bottom spray, top spray fluid bed processor by tangential spray, or top spray Flex Stream process.

Preparation of Carotenoid Beadlets by Formula 6

The process involves the preparation of carotenoid beadlets by extrusion and spheronization method. According to the process, carotenoid is dispersed in water to form a solution. The solution is further added to a powder blend of low viscosity HPMC polymer, sugar, surfactant(s), binder(s) and one or more other excipients. Mixing of carotenoids with the powder blend can be affected in a rapid mixing granulator and/or planetary mixer. After uniform mixing, the granules are extruded and spheronized to form beadlets. These uniform spherical beadlets core are further coated with a coating system of starch and antioxidant to form hydrophilic matrix beadlets of fat soluble carotenoids.

Dissolution Study for Formula 3

Dissolution testing is carried out to check release of lutein from carotenoids beadlets by determining the amount of lutein that goes into testing media as a function of time. USP type II (Paddle) apparatus was employed using dissolution medium volume 900 ml with rate of agitation as 50 rpm and water with 0.25% SLS as dissolution medium.

TABLE 2

Dissolution Profile for beadlets of Instant Invention

| Time (Minutes) | Mean (%) Release lutein from Formula 3 |
|---|---|
| 10 | 96.9 |
| 20 | 101.11 |
| 30 | 94.02 |
| 60 | 101.16 |
| 90 | 101.54 |

The dissolution study of formula 3 in water with 0.25% sodium lauryl sulphate exhibits more than 90% lutein release within 10 minutes.

With further reference to Table 1, the seven compositions are reported. Formula 3 represents one example of one particularly optimized formula for the layering process, while formula 6 represents one example of one particularly optimized formula for the extrusion spheronization process. Of these two formulas the dissolution study was carried out with formula 3 and further described below.

In a dissolution profile for another batch of formula 3, release of both the carotenoids in the composition-lutein and zeaxanthin were studied. See Table A.

Methodology:

Dissolution testing parameters include: 1. System—Electrolab; 2. USP Apparatus II (Paddle); 3. Speed [rpm] 50; 4. Medium: 0.25% SLS in Water; 5. Volume [mL]: 900.0; 6. Medium Temperature [° C.] 37.0±0.5; and 7. Sampling Times [min] 10, 20, 30, 60, and 90.

TABLE A

| Time (Min) | Formula 3 (another batch) | |
|---|---|---|
| | Mean (%) Release of Lutein | Mean (%) Release of Zeaxanthin |
| 0 | 0 | 0 |
| 10 | 97.03 | 93.30 |
| 20 | 104.01 | 98.37 |
| 30 | 102.93 | 102.42 |
| 60 | 104.15 | 104.30 |
| 90 | 109.81 | 106.61 |

Figure 7:
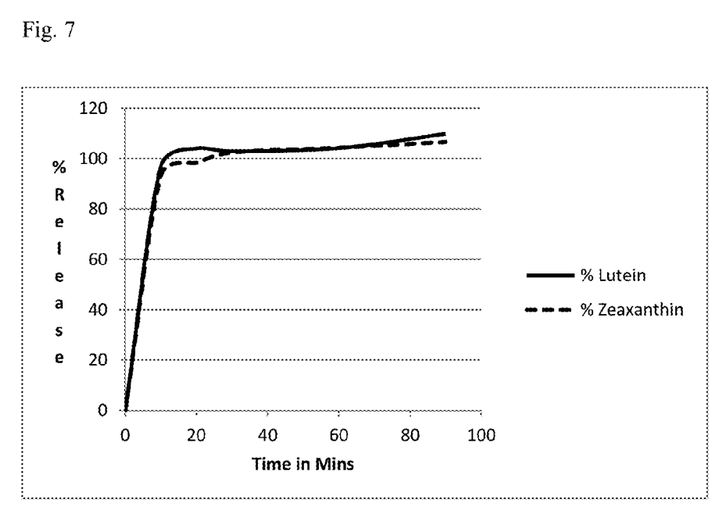
FIG. 7 shows a dissolution profile of Formula 3 over time.

In FIG. 7, the dissolution study in water with 0.25% Sodium lauryl sulphate showed more than 90.0% release within 10 min.

Stability Study of Formula 3

Accelerated stability study of formula 3 was carried out for three batches with reproducibility at the same formula at 40° C.±2° C./75% relative humidity? (RH)±5% RH for the period of 6 months. Product was packed in a sealed aluminium pouch and incubated in stability chambers.

TABLE 3

Lutein content of beadlets during stability study

| Formula 3 | Initial Assay (lutein content) | Assay after 3 Months (lutein content) | Assay after 6 Months (lutein content) |
|---|---|---|---|
| Batch 1 | 6.54 | 6.33 | 6.16 |
| Batch 2 | 6.67 | 6.41 | 6.23 |
| Batch 3 | 6.42 | 6.14 | 6.13 |

Accelerated stability study at 40° C.±2° C./75% RH±5% RH showed that the hydrophilic matrix composition of the present invention is stable over a period of 6 months with respect to the lutein content of the beadlets. Further no physical or colour change was observed after 6 month accelerated stability study.

Further stability study results are shown in Table B.

TABLE B

| Batch No | Initial Assay (%) | | Assay after 3 Months (%) | | Assay after 6 Months (%) | |
|---|---|---|---|---|---|---|
| | Lutein | Zeaxanthin | Lutein | Zeaxanthin | Lutein | Zeaxanthin |
| Formula 1 | 6.54 | 1.41 | 6.33 | 1.15 | 6.16 | 1.18 |
| Formula 2 | 6.67 | 1.38 | 6.41 | 1.22 | 6.23 | 1.21 |
| Formula 3 | 6.42 | 1.38 | 6.14 | 1.29 | 6.13 | 1.15 |

Table B shows stability studies to include other fat soluble nutrient other than lutein in this specification, in particular with inclusion of zeaxanthin.

Accelerated stability study at 40° C.±2° C./75% RH±5% RH for the period of 6 months showed that the beadlets were stable with respect to Lutein and Zeaxanthin content and no physical or color change observed after 6 months accelerated stability study.

Example 3

Formulation of Tablets Using Carotenoid Beadlets

TABLE 4

Composition of tablets containing beadlets

| Sr. No. | Ingredients | Qty mg/tab |
|---|---|---|
| 1 | Beadlets of Formula 3 | 160 |
| 2 | Macrocrystalline cellulose | 630 |
| 3 | Vitamin premix | 130 |
| 4 | Sodium starch glycolate | 50 |
| 5 | Talc | 10 |
| 6 | Magnesium stearate | 10 |
| 7 | Total | 1000 |

Process for Preparation of the Tablets

Beadlets of formula 3, vitamin premix and other excipients are weighed as per the given formula. The vitamin premix and excipients except magnesium stearate are passed through a 40 mesh sieve and blended well in a suitable blender. Weighed amount of beadlets are added in the above blend and mixed further for 10 minutes. The blend is lubricated with magnesium stearate and talc. The lubricated blend is compressed in tablets with hardness of 7-9 kg/cm$^2$.

Stability Study of the Tablets

The tablets obtained from three reproducible batches using formula of example 3 are packed in sealed aluminium pouch and incubated in stability chambers. Accelerated stability study was carried out at 40° C.±2° C./75% RH±5% RH for the period of 6 months.

TABLE 5

Lutein content in tablets during stability study

| Batch No | Initial Assay (lutein content) | Assay after 3 months (lutein content) | Assay after 6 months (lutein content) |
|---|---|---|---|
| Batch 1 | 7.08 | 6.55 | 6.35 |
| Batch 2 | 7.47 | 7.11 | 6.88 |
| Batch 3 | 7.49 | 7.11 | 6.74 |

It was found that the tablet formulations prepared using beadlets of formula 3 are stable over the period of 6 months with respect to lutein content. Further no physical or colour change was observed in the tablet formulation during this accelerated stability study.

Comparative Bioavailability Study (for Formula 3)

A randomized, double blind, three-treatment, single-period, single dose, parallel, comparative bioavailability study of the composition of the instant invention in the form of hydrophilic matrix beadlets 20 mg/capsule was carried out with the marketed reference product in 14 healthy, human, adult subjects under fed conditions.

Mean AUC and Cmax values obtained for 14 volunteers using both the test product T (e.g. Formula 3) and marketed reference product (R) are as follows:

TABLE 6

Pharmacokinetic data for Lutein from test and reference product

| Products | Cmax | AUC24 | AUC48 | AUC72 | AUC168 | AUCt |
|---|---|---|---|---|---|---|
| T | 824.75 | 7427.69 | 18318.06 | 26697.99 | 53983.48 | 53343.69 |
| R | 773.95 | 5179.50 | 14208.09 | 19985.64 | 38581.13 | 35004.44 |
| Fold increase | 1.06 | 1.43 | 1.29 | 1.33 | 1.39 | 1.52 |

Cmax and AUC values for test product (T) as per above data points indicate that hydrophilic matrix beadlets of the instant invention exhibit about 1.6 times higher bioavailability than the marketed reference product (R).

Figure 2:
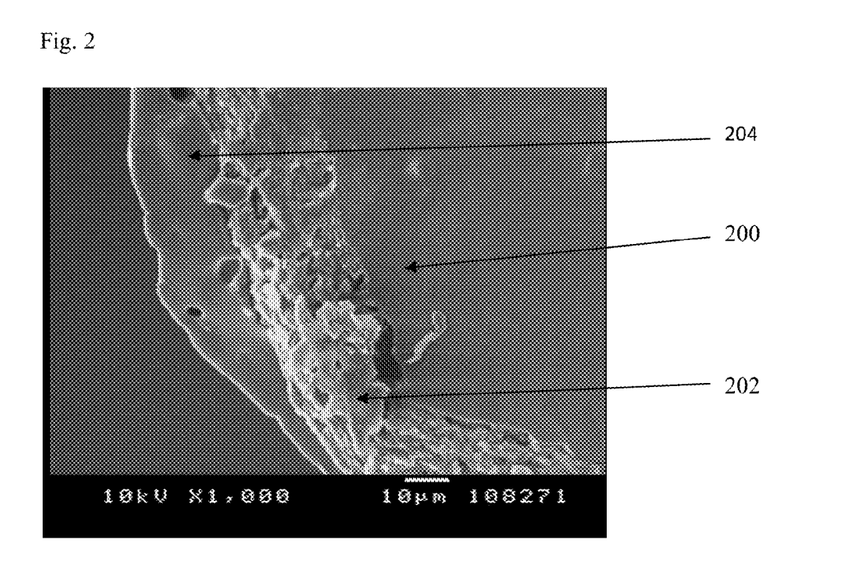
FIG. 2 shows a micrograph of a matrix from a SEM, of beadlets of Formula 3 and prepared by a layering process.
Figure 3:
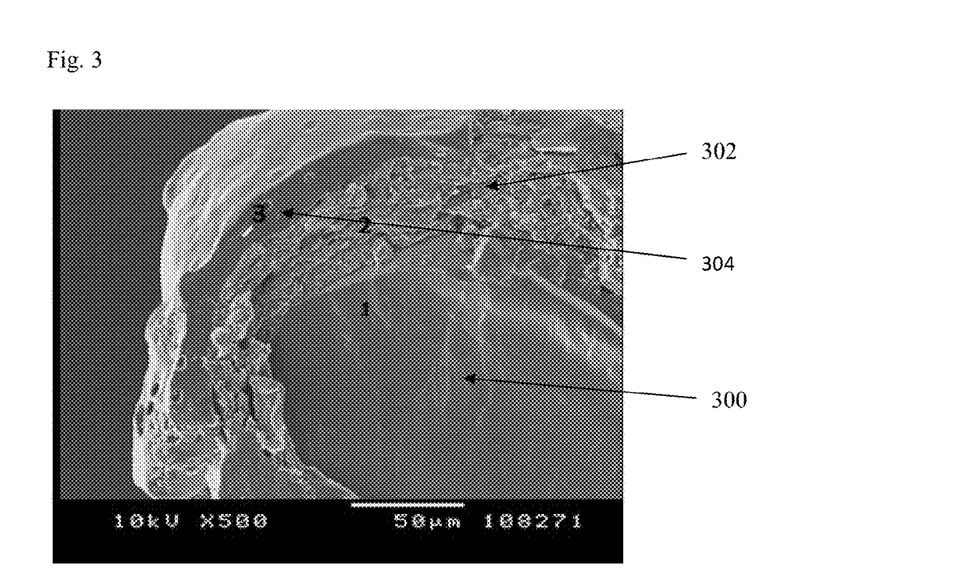
FIG. 3 shows a micrograph of a matrix from a SEM, of beadlets of Formula 3 and prepared by a layering process.
Figure 4:
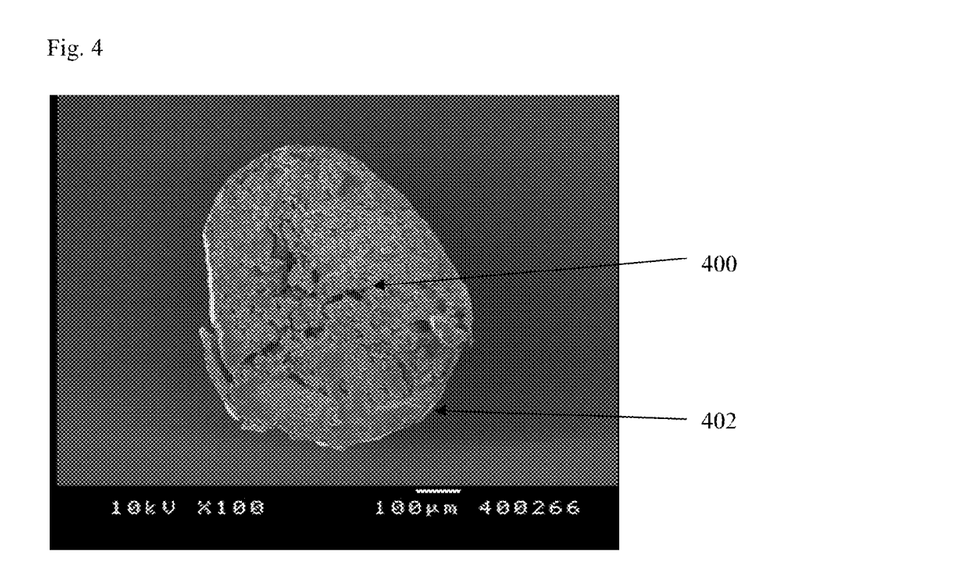
FIG. 4 shows a micrograph of a matrix from a SEM, of beadlets of Formula 6 and prepared by an extrusion and spheronization process.
Figure 5:
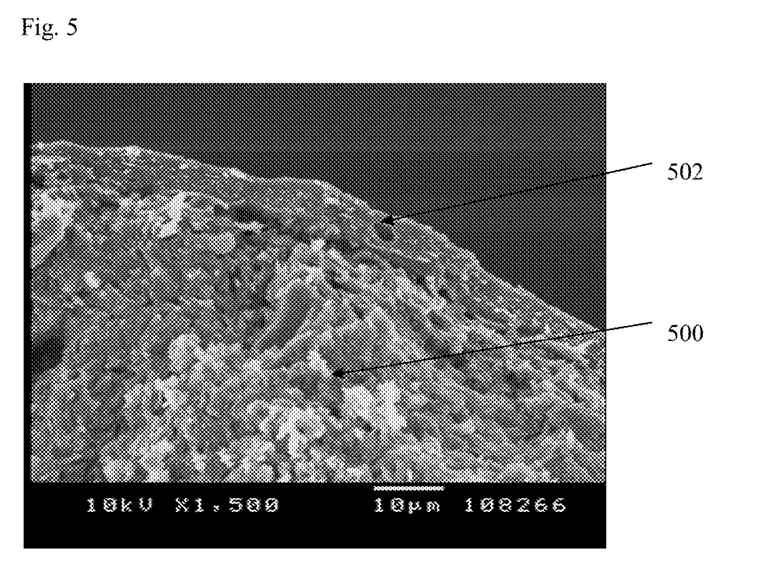
FIG. 5 shows a micrograph of a matrix from a SEM, of beadlets of Formula 6 and prepared by an extrusion and spheronization process.
Figure 6:
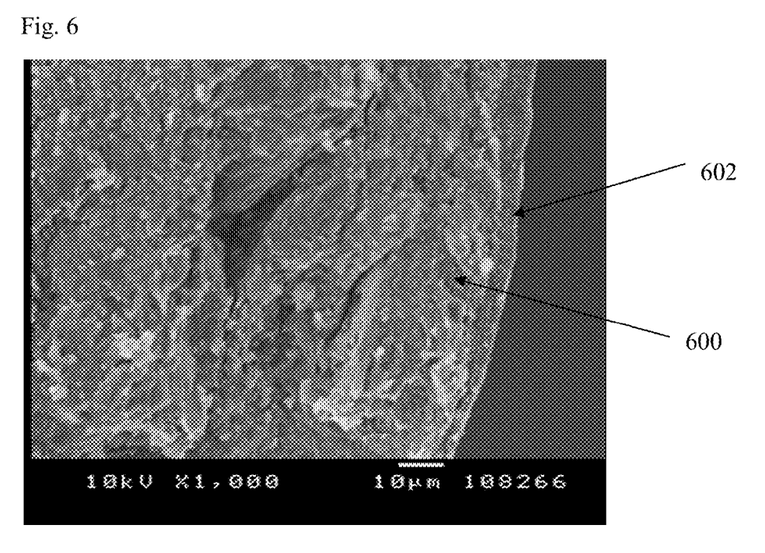
FIG. 6 shows a micrograph of a matrix from a SEM, of beadlets of Formula 6 and prepared by an extrusion and spheronization process.

FIGS. 1 to 6 show matrix structures evaluated by SEM analysis to check embedding of active within the hydrophilic low viscosity polymer. This was done for matrix beadlets prepared by both layering inert spheres (FIGS. 1 to 3) and by an extrusion spheronization method (FIGS. 4 to 6). The cross-section morphologies were visualized using Scanning Electron Microscope (JSM-5400, JEOL, Japan). The samples were mounted on a brass stub using double sided tape and then sputtered with a thin layer of gold using Sputter coater (JEOL-JEC550-twin coater, Japan). The photographs were taken at an acceleration voltage of 10 kV.

Figure 1:
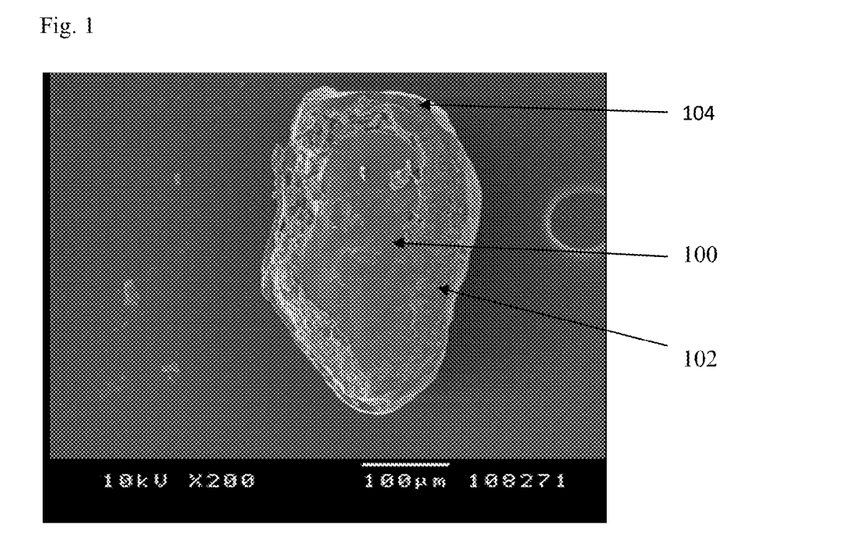
FIG. 1 shows a micrograph of a matrix structure from a scanning electron microscope (SEM), of beadlets of Formula 3 and prepared by a layering process.

FIG. 1 is a cross section of a beadlet, which clearly show the layer of the hydrophilic matrix 102 containing carotenoids and cellulose polymer on an inert core 100 and an outer coating 104 having a protective layer of starch and antioxidant on top of it.

FIG. 2 is a sectional close up view of a beadlet, which gives a clear view of two layers on inert core 200 (centre). First layer 202 on inert core is of carotenoid and cellulose polymer matrix and second is a protective layer 204.

FIG. 3 is another sectional close up view of a beadlet showing: 1. inert core 300; 2. carotenoid—low viscosity cellulose polymer matrix 302; and 3. protective layer of starch 304.

FIG. 4 shows a micrograph of a matrix from a SEM, of beadlets of Formula 6 and prepared by an extrusion and spheronization process. The SEM image is a section of a beadlet showing a centre core 400 of a carotenoid matrix with a low viscosity cellulose polymer, which is prepared by extrusion and spheronization, and also having thin film of protective layer 402 on about it.

FIG. 5 is a micrograph of a matrix from a SEM, of beadlets of Formula 6 and prepared by an extrusion and spheronization process, which shows the hydrophilic matrix 500 of a fat soluble nutrient, e.g. carotenoid, and a low viscosity polymer, e.g. low viscosity cellulose, and the outer coating 502, which may be a protective coating. FIG. 6 is a micrograph of a matrix from a SEM, of beadlets of Formula 6 and prepared by an extrusion and spheronization process, which shows the hydrophilic matrix 600 of a fat soluble nutrient, e.g. carotenoid, and a low viscosity polymer, e.g. low viscosity cellulose, and the outer coating 602, which may be a protective coating. The SEM images in FIGS. 5 and 6 gives a clearer picture certain distinct parts of the beadlet, namely the centre core of carotenoid matrix in which is embedded in a cellulose polymer. This matrix is coated with a protective layer.

Effect of Hydrophilic Matrix on Dispersibility of Lipophilic Beadlets

Objective: To demonstrate the effect of the hydrophilic matrix herein (e.g. using a low viscosity HPMC) on dispersibility of beadlets in comparison with ordinary matrix as well as matrix of high viscosity cellulose polymer.

Experiment Plan:

The trials were set up in an effort to exhibit the effects of a hydrophilic matrix herein. In the trials shown, a low viscosity hydroxypropyl methyl cellulose (HPMC), having viscosity in the range of 1 to 5 Cps is used, and in the ratio of 1:0.5 to 1:1.5 being the ratio of fat soluble nutrient:hydrophilic polymer.

The experiment was carried out to check effect of matrix component on dispersibility of beadlets in liquid vehicle.

Beadlets were prepared as per the formula of Trial 1 to 6 using the process as described herein. Details of trials are as follows in Table C and Table D:

TABLE C

| Sr. No | Batch No | Matrix type | Matrix polymer |
|---|---|---|---|
| 1 | Trial 1 | Matrix of high viscosity HPMC 15 cP in ratio 1:0.5 | HPMC-E15 |
| 2 | Trial 2 | Matrix of high viscosity HPMC 15 cP in ratio 1:1.5 | HPMC-E15 |
| 3 | Trial 3 | Ordinary matrix of starch in ratio 1:0.5 | Starch |
| 4 | Trial 4 | Ordinary matrix of starch in ratio 1:1.5 | Starch |
| 5 | Trial 5 | low viscosity polymer HPMC in ratio 1:0.15 (low amount of HPMC to prepare non-matrix beadlets) | HPMC VLV* |
| 6 | Trial 6 | Matrix of low viscosity HPMC of the invention as per ratio claimed in the invention | HPMC VLV |

HPMC VLV: Hydroxypropyl methyl cellulose very low viscosity 2.5 cP

Ratio described above is Lipophilic active:matrix polymer

Trial 1 and 2 represent use of polymer matrix which is hydrophilic (HPMC), but having higher viscosity than the ranges of a hydrophilic matrix herein, to check effect of viscosity of polymer matrix on dispersibility of beadlets in liquid media. It is used in two different ratios such as 1:0.5 and 1:1.5.

Trial 3 and 4 represent use of starch matrix, which is not hydrophilic like HPMC, and is employed in the same two ratios as above to check the effect of ordinary matrix on dispersibility of beadlets in liquid media.

Trial 5 represents use of HPMC polymer of low viscosity in very low amounts such that these would not be considered suitable to form a matrix. Trial 5 is to demonstrate the significance of having an "effective amount" of hydrophilic matrix on enhanced dispersibility and drug release.

Trial 6 represents beadlets made according to the principles herein, wherein low viscosity polymer HPMC is used in effective amount to affect beadlet dispersibility and drug release.

TABLE D

| Ingredients | Trial 1 | Trial 2 | Trial 3 | Trial 4 | Trial 5 | Trial 6 |
|---|---|---|---|---|---|---|
| | | | Batch no | | | |
| | | | Qty in (g) | | | |
| NPS (60-80#) | 0.495 | 0.381 | 0.495 | 0.381 | 0.535 | 0.437 |
| Lutein | 0.114 | 0.114 | 0.114 | 0.114 | 0.114 | 0.114 |
| Starch | 0.000 | 0.000 | 0.057 | 0.171 | 0.000 | 0.000 |
| HPMC-E15 | 0.057 | 0.171 | 0.000 | 0.000 | 0.000 | 0.000 |
| Methocel VLV | 0.000 | 0.000 | 0.000 | 0.000 | 0.017 | 0.114 |
| Ascorbyl Palmitate | 0.013 | 0.013 | 0.013 | 0.013 | 0.013 | 0.013 |
| Tocopherol mix | 0.036 | 0.036 | 0.036 | 0.036 | 0.036 | 0.036 |
| Tween 80 | 0.083 | 0.083 | 0.083 | 0.083 | 0.083 | 0.083 |
| Kollidon CL-F | 0.020 | 0.020 | 0.020 | 0.020 | 0.020 | 0.020 |
| SLS | 0.012 | 0.012 | 0.012 | 0.012 | 0.012 | 0.012 |
| Talc | 0.006 | 0.006 | 0.006 | 0.006 | 0.006 | 0.006 |
| Aerosil 200 | 0.006 | 0.006 | 0.006 | 0.006 | 0.006 | 0.006 |
| Starch K4484 | 0.140 | 0.140 | 0.140 | 0.140 | 0.140 | 0.140 |
| Sodium Ascorbate | 0.011 | 0.011 | 0.011 | 0.011 | 0.011 | 0.011 |
| Talc | 0.007 | 0.007 | 0.007 | 0.007 | 0.007 | 0.007 |
| MDC | 3.422 | 3.422 | 0.000 | 0.000 | 2.000 | 3.422 |
| IPA | 0.280 | 0.280 | 0.280 | 0.280 | 0.280 | 0.280 |
| Acetone | 0.450 | 0.450 | 0.000 | 0.000 | 0.450 | 0.450 |
| Purified Water | 0.264 | 0.264 | 1.900 | 2.264 | 0.264 | 0.264 |
| Batch Size | 1.000 | 1.000 | 1.000 | 1.000 | 1.000 | 1.000 |

Dispersibility of Beadlets

To study the effect of dispersibility of beadlets, 100 mg of beadlets were added to 200 ml of water at 500 rpm. The initial photographs immediately after dispersing beadlets in water (0 minute) were recorded and after dispersion of beadlets, evidenced in the form of coloured liquid medium, the time is noted and again photographs are recorded.

Observation in the form of Photographs (FIGS. 8A to 13B)

Figure 8A:
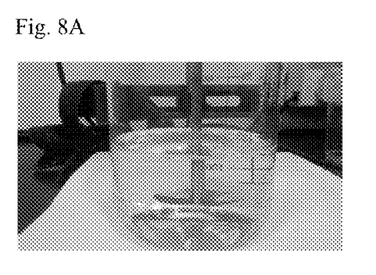
FIGS. 8A and B show beadlets from a trial 1: beadlets with high viscosity HPMC 15 cP matrix (ratio of lipophilic active to polymer is 1:0.5).
Figure 8B:
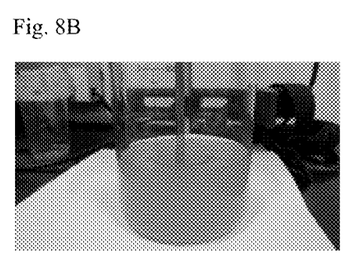

FIGS. 8A and B show beadlets from a trial 1: beadlets with high viscosity HPMC 15 cP matrix (ratio of lipophilic active to polymer is 1:0.5). FIG. 8A shows a 0 minute photograph, and FIG. 8B shows a photograph after 18 minutes.

Figure 9A:
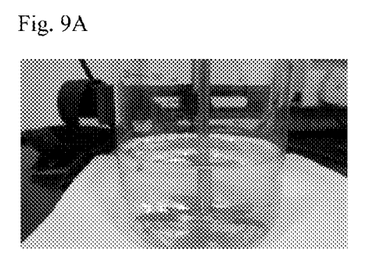
FIGS. 9A and B show beadlets from trial 2: beadlets with high viscosity HPMC 15 cP matrix (ratio of lipophilic active to polymer is 1:1.5).
Figure 9B:
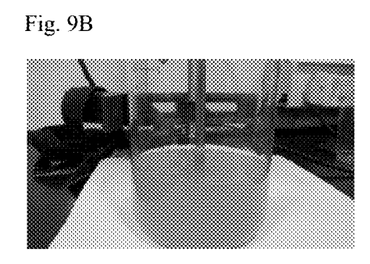

FIGS. 9A and B show beadlets from trial 2: beadlets with high viscosity HPMC 15 cP matrix (ratio of lipophilic active to polymer is 1:1.5). FIG. 9A shows a 0 minute photograph, and FIG. 8B shows a photograph after 4 minutes 28 seconds.

Figure 10A:
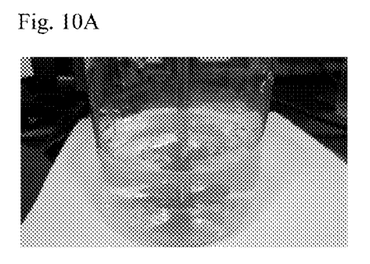
FIGS. 10A and B show beadlets from trial 3: beadlets with ordinary (non-hydrophilic) starch matrix (ratio of lipophilic active to starch is 1:0.5)
Figure 10B:
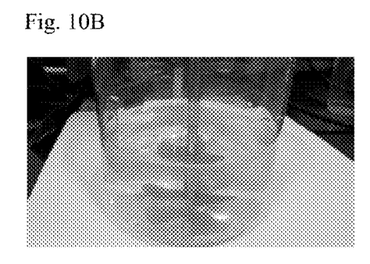

FIGS. 10A and B show beadlets from trial 3: beadlets with ordinary (non-hydrophilic) starch matrix (ratio of lipophilic active to starch is 1:0.5). FIG. 10A shows a 0 minute photograph, and FIG. 10B shows a photograph after 25 minutes.

Figure 11A:
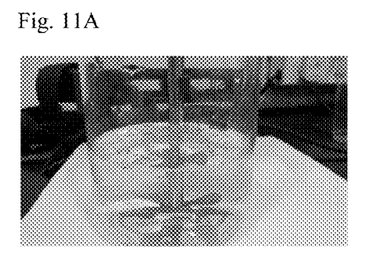
FIGS. 11A and B show beadlets from trial 4: beadlets with ordinary (non-hydrophilic) starch matrix (ratio of lipophilic to starch is 1:1.5)
Figure 11B:
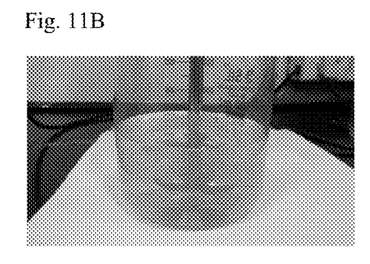

FIGS. 11A and B show beadlets from trial 4: beadlets with ordinary (non-hydrophilic) starch matrix (ratio of lipophilic to starch is 1:1.5). FIG. 11A shows a 0 minute photograph, and FIG. 11B shows a photograph after 20 minutes.

Figure 12A:
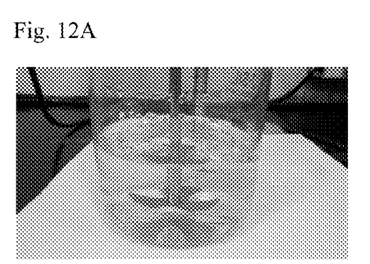
FIGS. 12A and B show beadlets from trial 5: beadlets with low viscosity HPMC 2.5 cP matrix (ratio of lipophilic nutrient to polymer is 1:0.15), which is not an effective amount for a hydrophilic matrix.
Figure 12B:
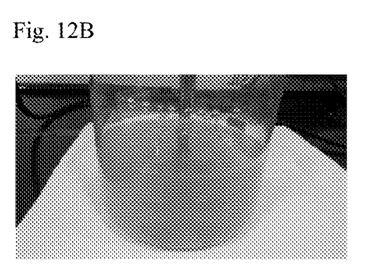

FIGS. 12A and B show beadlets from trial 5: beadlets with low viscosity HPMC 2.5 cP matrix (ratio of lipophilic nutrient to polymer is 1:0.15), which is not an effective amount for a hydrophilic matrix. FIG. 12A shows a 0 minute photograph, and FIG. 12B shows a photograph after 3 minutes, 45 seconds.

Figure 13A:
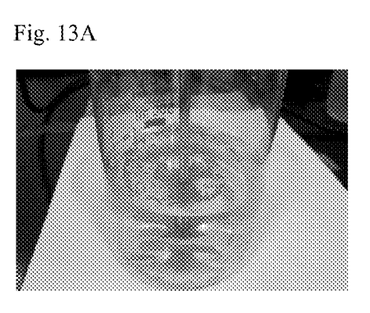
FIGS. 13A and B show beadlets from trial 6: beadlets made by the principles and concepts herein using a low viscosity HPMC in a ratio of 1:1 (lipophilic nutrient to polymer).
Figure 13B:
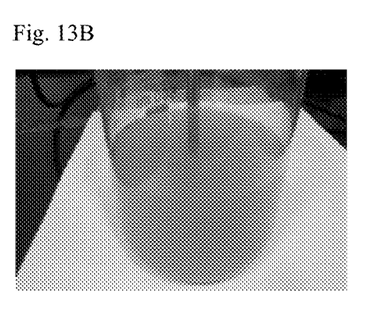

FIGS. 13A and B show beadlets from trial 6: beadlets made by the principles and concepts herein using a low viscosity HPMC in a ratio of 1:1 (lipophilic nutrient to polymer). FIG. 13A shows a 0 minute photograph, and FIG. 13B shows a photograph after 30 seconds.

Observation

| Sr. No | Batch No | Composition type | Dispersion time | Comment |
|---|---|---|---|---|
| 1 | Trial 1 | 1:0.5 HPMC-E15 | 18 min | Complete dispersion was observed |
| 2 | Trial 2 | 1:1.5 HPMC-E15 | 4 min 28 sec | Complete dispersion was observed |
| 3 | Trial 3 | 1:0.5 Starch | 25 min | Not completely dispersed |
| 4 | Trial 4 | 1:1.5 Starch | 20 min | Not completely dispersed |
| 5 | Trial 5 | 1:0.15 Methocel VLV | 3 min 45 sec | Complete dispersion was observed |
| 6 | Trial 6 | 1:1 Methocel VLV | 30 sec | Complete dispersion was observed |

Observation as Per Batches.

1. Trial 1 (1:0.5 HPMC-E15):—Initially beadlets were disintegrated into small fragments followed by slow release of lutein in water. The complete release of drug was observed in 18 min.
2. Trial 2 (1:1.5 HPMC-E15):—Disintegration of beadlets and release of drug occurs at the same point and complete release of drug occurs at 4 min 28 sec.
3. Trial 3 (1:0.5 Starch):—Beadlets were intact for about 10-15 min followed by disintegration of beadlets into smaller particles complete dispersion of beadlets and release of drug was not observed.
4. Trial 4 (1:1.5 Starch):—Beadlets were intact for about 10-15 min followed by disintegration of beadlets into smaller particles complete dispersion of beadlets and release of drug was not observed
5. Trial 5 (1:0.15 Methocel VLV):—Beadlets releases the drug as soon as it comes in contact with water and complete dispersion was observed in 3 min 45 sec
6. Trial 6 (1:1 Methocel VLV):—Complete release was observed within 30 sec.

Conclusion:—
  Beadlets with Hydrophilic matrix polymer with low viscosity, such as for example a cellulose containing polymer can exhibit good dispersibility and drug release as compared to ordinary (non-hydrophilic polymer such as starch).
  Beadlets of hydrophilic matrix polymer having low viscosity, when employed in effective amount (ratio such as 1:0.5 to 1:1.5) can exhibit excellent dispersibility and drug release as compared to lower amounts of hydrophilic matrix polymer having low viscosity.
  Beadlets of hydrophilic matrix polymer having low viscosity (1 to 5 cP) can be advantageous over hydrophilic matrix polymer having higher viscosity such as 15 cP.

The above trials are reported to show that hydrophilic matrix polymers of low viscosity in effective amounts confer beadlets with enhanced dispersibility and drug release.

The experimental results, data, and trials herein are to help show the use of effective amounts of hydrophilic matrix of low viscosity polymers in certain ratio of 1:0.5 to 1:1.5 (ratio of lipophilic active:hydrophilic matrix polymer).

Aspects

Any of aspects may be combined with any of aspects.

1. Hydrophilic matrix beadlet compositions with enhanced bioavailability comprising; at least one fat soluble nutrient; effective amount of cellulose polymer with low viscosity; and at least one more pharmaceutically acceptable excipient.
2. Hydrophilic beadlet compositions of aspect 1, wherein fat soluble nutrient is selected from carotenoids, vitamins, omega fatty acids, glycerides, capsaicin, curcumin, extracts of Salacia, Terminalia, Co-Enzyme Q-10, Ubiquinol and mixtures thereof.
3. Hydrophilic beadlet compositions of aspect 2, wherein fat soluble carotenoid nutrient is selected from the group consisting of lutein, lutein esters, alpha carotene, beta-carotene, zeaxanthin, mesozeaxanthin, betacryptoxanthin, zeaxanthin esters, astaxanthin, lycopene and mixtures thereof.
4. Hydrophilic beadlet compositions of any of aspects 1 to 3, wherein fat soluble carotenoid nutrient is comprised of lutein and zeaxanthin in the ratio of 4.5:1 to 5.5:1.
5. Hydrophilic beadlet compositions of any of aspects 1 to 4, at least one cellulose polymer excipient with low viscosity is selected from methyl cellulose, carboxymethyl cellulose, hydroxyethyl cellulose, hydroxypropyl cellulose, and hydroxypropyl methyl cellulose or mixture thereof.
6. Hydrophilic beadlet compositions of any of aspects 1 to 5, wherein at least one cellulose polymer has viscosity in the range of 1 to 5 cps.
7. Hydrophilic beadlet compositions of any of aspects 1 to 6, wherein at least one cellulose polymer is hydroxypropyl methyl cellulose having viscosity of 2.5 cps.
8. Hydrophilic beadlet composition of any of aspects 1 to 7, wherein ratio of fat soluble nutrient to cellulose polymer with low viscosity is about 1:0.5 to 1:1.5.
9 Hydrophilic beadlet composition of any of aspects 1 to 8, wherein fat soluble nutrient is present in an amount of about 5 to about 25% by weight of beadlets.
10. Hydrophilic beadlet composition of any of aspects 1 to 9, further comprising at least one pharmaceutically acceptable excipient such as inert core, diluents, antioxidants, surfactants, disintegrant, glidant, coating agent or mixtures thereof.
11. A process for preparation of hydrophilic beadlet compositions with enhanced bioavailability, which is comprised of
i. Suspending fat soluble nutrient in non-polar solvent and diluting the resulting suspension with polar solvent;
ii. Adding at least one pharmaceutically acceptable excipient such as antioxidant, surfactant, disintegrant, solubility enhancer or the mixture thereof to step i suspension by using homogenizer;
iii. Dispersing low viscosity hydroxypropyl methyl cellulose in polar solvent;
iv. Adding hydroxypropyl methyl cellulose dispersion to fat soluble nutrient suspension of step ii in presence of at least one excipient to form matrix beadlets; and
v. Drying the resulting beadlets and coating with non-functional coat of polysaccharides.
12. A process for hydrophilic beadlet compositions of aspect 11, wherein at least one excipient is selected from the group of sucrose, sugar, microcrystalline cellulose, tartaric acid, mannitol, maltodextrin, starch, modified starch or combination thereof.
13. A process for hydrophilic beadlet compositions of aspect 11 or 12, wherein beadlets are formed by fluid bed coating or extrusion spheronization.
14. Hydrophilic matrix compositions of any of aspects 1 to 13, wherein the oral bioavailability of beadlets is at least 1.6 times higher than the marketed reference composition containing fat soluble nutrients.

We claim:
1. A hydrophilic matrix beadlet composition with enhanced bioavailability comprising:
at least one fat soluble nutrient;
an effective amount of at least one cellulose polymer with low viscosity,
the at least one fat soluble nutrient and the effective amount of the at least one cellulose polymer with low viscosity are formed into a matrix exhibiting a hydrophilic property, where the at least one cellulose polymer with low viscosity has a viscosity in the range of 1 to 5 cps, and a ratio of the at least one fat soluble nutrient to the at least one cellulose polymer with low viscosity is about 1:0.5 to 1:1.5; and
at least one pharmaceutically acceptable excipient.
2. The hydrophilic beadlet composition of claim 1, wherein the at least one fat soluble nutrient is selected from a carotenoid, vitamin, omega fatty acid, glyceride, capsaicin, curcumin, extract of Salacia, extract of Terminalia, Co-Enzyme Q-10, Ubiquinol and mixtures thereof.
3. The hydrophilic beadlet composition of claim 2, wherein the carotenoid is selected from the group consisting of lutein, lutein esters, alpha carotene, beta-carotene, zeaxanthin, mesozeaxanthin, betacryptoxanthin, zeaxanthin esters, astaxanthin, lycopene and mixtures thereof.
4. The hydrophilic beadlet composition of claim 3, wherein the carotenoid is comprised of lutein and zeaxanthin in the ratio of 4.5:1 to 5.5:1.
5. The hydrophilic beadlet composition of claim 1, wherein the at least one cellulose polymer with low viscosity is selected from methyl cellulose, carboxymethyl cellulose, hydroxyethyl cellulose, hydroxypropyl cellulose, and hydroxypropyl methyl cellulose or mixture thereof.
6. The hydrophilic beadlet composition of claim 5, wherein the at least one cellulose polymer with low viscosity is hydroxypropyl methyl cellulose having a viscosity of 2.5 cps.
7. The hydrophilic beadlet composition of claim 1, wherein the at least one fat soluble nutrient is present in an amount of about 5 to about 25% by weight of the composition.
8. The hydrophilic beadlet composition of claim 1, wherein the at least one pharmaceutically acceptable excipient is selected from a inert core, diluent, antioxidant, surfactant, disintegrant, glidant, coating agent or mixtures thereof.
9. The hydrophilic beadlet composition of claim 1, wherein the composition exhibits increased oral bioavailability relative to a composition including a fat soluble nutrient and polymer and which does not include the matrix exhibiting a hydrophilic property of claim 1.
10. The hydrophilic beadlet composition or claim 1, wherein the matrix exhibiting a hydrophilic property is formed as a core of the composition.

* * * * *